(12) United States Patent
Ozaki et al.

(10) Patent No.: US 9,858,662 B2
(45) Date of Patent: Jan. 2, 2018

(54) IMAGE PROCESSING DEVICE, COMPUTER STORAGE MEDIUM, AND METHOD FOR DETECTING AND DISPLAYING NUCLEATED TARGET CELLS

(71) Applicant: FUJI XEROX CO., LTD., Tokyo (JP)

(72) Inventors: Ryota Ozaki, Yokohama (JP); Noriji Kato, Yokohama (JP); Hideto Oda, Yokohama (JP); Yukio Kumazawa, Yokohama (JP)

(73) Assignee: FUJI XEROX CO., LTD., Tokyo (JP)

( * ) Notice: Subject to any disclaimer, the term of this patent is extended or adjusted under 35 U.S.C. 154(b) by 0 days.

(21) Appl. No.: 14/826,825

(22) Filed: Aug. 14, 2015

(65) Prior Publication Data
US 2015/0356731 A1 Dec. 10, 2015

Related U.S. Application Data

(63) Continuation of application No. PCT/JP2013/080050, filed on Nov. 6, 2013.

(30) Foreign Application Priority Data

May 31, 2013 (JP) .................................. 2013-115423

(51) Int. Cl.
*G06T 7/00* (2017.01)
*G06K 9/00* (2006.01)
(Continued)

(52) U.S. Cl.
CPC ....... *G06T 7/0012* (2013.01); *G01N 15/1475* (2013.01); *G02B 21/367* (2013.01);
(Continued)

(58) Field of Classification Search
CPC ............... G06T 7/0012; G06T 7/0081; G06T 2207/10024; G06T 2207/10056;
(Continued)

(56) References Cited

U.S. PATENT DOCUMENTS 6,330,350 B1 * 12/2001 Ahn .................... G01N 15/1475
382/134
7,907,769 B2 * 3/2011 Sammak ............ G06K 9/00127
382/133
(Continued)

FOREIGN PATENT DOCUMENTS

CN  101226155 A  7/2008
CN  101719278 A  6/2010
(Continued)

OTHER PUBLICATIONS

NPL, Yosuke Shimizu, Hotta S..: Detection and Retrieval of Nucleated Red Blood Cells Using Linear Subspaces, 2011, 67-73.*
(Continued)

*Primary Examiner* — Sean Conner
*Assistant Examiner* — Pinalben Patel
(74) *Attorney, Agent, or Firm* — Oliff PLC

(57) ABSTRACT

A device comprises: a nucleus-candidate-region extracting section that extracts, from a captured image obtained by image-capturing a sample piece including a target cell having a nucleus, a nucleus candidate region corresponding to the nucleus; a basic-probability-information acquiring section that acquires, for each of a plurality of determination subject regions determined on the basis of the nucleus candidate region extracted by the nucleus-candidate-region extracting section, basic probability information indicating probability that an image in the determination subject region is an image of the target cell, on the basis of a feature amount of the image of the determination subject region; and a probability-information calculating section that calculates probability information indicating probability that an image in a display subject region corresponding to the nucleus candidate region is the image of the target cell, on the basis (Continued)

of the basic probability information acquired for each of the plurality of determination subject regions.

8 Claims, 7 Drawing Sheets

(51) Int. Cl.
*G01N 15/14* (2006.01)
*G02B 21/36* (2006.01)
*G06K 9/46* (2006.01)

(52) U.S. Cl.
CPC ....... *G06K 9/0014* (2013.01); *G06K 9/00523* (2013.01); *G06K 9/4647* (2013.01); *G06T 2207/10024* (2013.01); *G06T 2207/10056* (2013.01); *G06T 2207/20076* (2013.01); *G06T 2207/30024* (2013.01); *G06T 2210/41* (2013.01)

(58) Field of Classification Search
CPC . G06T 2207/20076; G06T 2207/20148; G06T 2207/30024; G06T 2210/41; G01N 15/1475; G02B 21/367; G06K 9/0014; G06K 9/00523; G06K 9/4647
See application file for complete search history.

(56) References Cited

U.S. PATENT DOCUMENTS

| | | | |
|---|---|---|---|
| 8,426,122 B2* | 4/2013 | Parikh | C12Q 1/6806 435/2 |
| 8,484,572 B2 | 7/2013 | Yamada | |
| 2003/0086134 A1 | 5/2003 | Enomoto | |
| 2005/0031183 A1* | 2/2005 | Wrigglesworth | G06T 7/20 382/133 |
| 2009/0087074 A1 | 4/2009 | Wong et al. | |
| 2009/0116705 A1 | 5/2009 | Suzuki et al. | |
| 2010/0098317 A1 | 4/2010 | Kiyuna | |
| 2010/0169811 A1 | 7/2010 | Yamada | |
| 2012/0004514 A1 | 1/2012 | Marugame | |
| 2012/0263369 A1* | 10/2012 | Xie | G06T 7/0012 382/134 |
| 2013/0163844 A1 | 6/2013 | Ozaki et al. | |
| 2014/0092228 A1 | 4/2014 | Usuba et al. | |
| 2014/0377753 A1* | 12/2014 | Bamford | G06T 7/0012 435/6.11 |

FOREIGN PATENT DOCUMENTS

| | | |
|---|---|---|
| CN | 102341703 A | 2/2012 |
| EP | 2719754 A1 | 4/2014 |
| JP | 2003-209683 A | 7/2003 |
| JP | 2004-248619 A | 9/2004 |
| JP | 2009-110486 A | 5/2009 |
| JP | 2010151647 A | 7/2010 |
| JP | 2012254042 A | 12/2012 |
| JP | 2013-128438 A | 7/2013 |
| WO | 2012/169088 A1 | 12/2012 |

OTHER PUBLICATIONS

Jul. 5, 2016 Office Action issued in Japanese Patent Application No. 2013-115423.
Feb. 18, 2014 International Search Report issued in International Patent Application No. PCT/JP2013/080050.
Feb. 18, 2014 Written Opinion of the International Searching Authority issued in International Patent Application No. PCT/JP2013/080050.
Ozaki et al., "Automatic Detection of Nucleated Red Blood Cells from Microscope Images using Cell-Hog Feature," Journal of the Japan Society of Precision Engineering, Nov. 5, 2013, vol. 79,No. 11, pp. 1074 to 1077.
Jul. 12, 2016 Office Action issued in Chinese Patent Application No. 201380074821.3.
Mar. 1, 2017 Search Report issued in European Patent Application No. 13885790.9.
Veillard et al, "SVM-based framework for the Robust Extraction of Objects from Histopathological Images Using Color, Texture, Scale and Geometry", Machine Learning and Applications. Dec. 12, 2012, pp. 70-75.
Yoshida, et al. "Image Processing for Drug Discovery Test with Cultured Cells", Jan. 1, 2008, pp. 31-33.

* cited by examiner

IMAGE OF DISPLAY SUBJECT REGION

RGB IMAGE    R IMAGE    G IMAGE    B IMAGE

IMAGE PROCESSING DEVICE, COMPUTER STORAGE MEDIUM, AND METHOD FOR DETECTING AND DISPLAYING NUCLEATED TARGET CELLS

CROSS REFERENCE TO RELATED APPLICATION

This is a continuation of International Application No. PCT/JP2013/080050 filed on Nov. 6, 2013, and claims priority from Japanese Patent Application No. 2013-115423, filed on May 31, 2013.

TECHNICAL FIELD

The present invention relates to an image processing device, a storage medium, and an image processing method.

SUMMARY OF INVENTION

According to an aspect of the invention, there is provided an image processing device including a nucleus-candidate-region extracting section that extracts, from a captured image obtained by image-capturing a sample piece including a target cell having a nucleus, a nucleus candidate region corresponding to the nucleus; a basic-probability-information acquiring section that acquires, for each of a plurality of determination subject regions determined on the basis of the nucleus candidate region extracted by the nucleus-candidate-region extracting section, basic probability information indicating probability that an image in the determination subject region is an image of the target cell, on the basis of a feature amount of the image of the determination subject region; and a probability-information calculating section that calculates probability information indicating probability that an image in a display subject region corresponding to the nucleus candidate region is the image of the target cell, on the basis of the basic probability information acquired for each of the plurality of determination subject regions.

Figure 1:
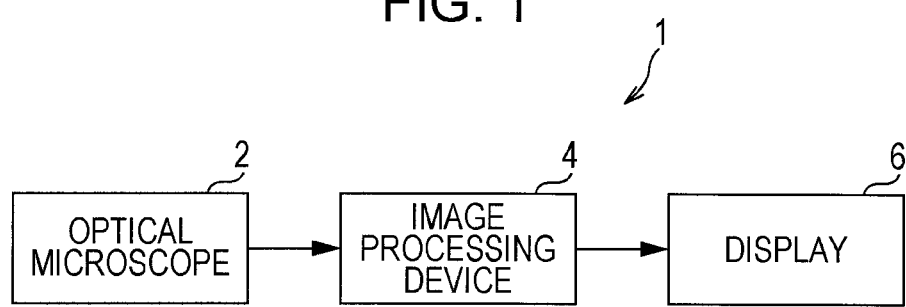
FIG. 1 is a system configuration diagram of an image processing system according to this exemplary embodiment.

REFERENCE SIGNS LIST 1 image processing device
2 optical microscope
4 image processing device
6 display
8 test-image acquiring unit
10 nucleus-candidate-region extracting unit
12 determination-subject-region setting unit
14 image-feature extracting unit
14a color-separation-image generating unit
14b Cell-HOG feature-amount extracting unit
14c feature selecting unit
16 reliability calculating unit
18 nucleated-red-blood-cell-candidate-region setting unit
20 display-subject-region setting unit
22 display-subject-region displaying unit
24 pixel block
26 nucleus candidate region
28 determination subject region
30 nucleated red blood cell candidate region
32 display subject region

DETAILED DESCRIPTION

An exemplary embodiment of the invention is described in detail below with reference to the drawings.

FIG. 1 shows a system configuration diagram of an image processing system 1 according to this exemplary embodiment. As shown in FIG. 1, the image processing system 1 includes an optical microscope 2, an image processing device 4, and a display 6. The image processing device 4 is connected with the optical microscope 2 and the display 6 so that data communication can be made.

The optical microscope 2 image-captures a sample piece on a slide glass arranged on a sample table by a CCD camera through an optical system such as an objective lens. In this exemplary embodiment, a sample in which maternal blood is applied to a slide glass and treated with May-Giemsa stain is used. Accordingly, a fetus-derived nucleated red blood cell in the maternal blood is dyed to bluish-violet color. The nucleated red blood cell is called target cell.

Figure 2:
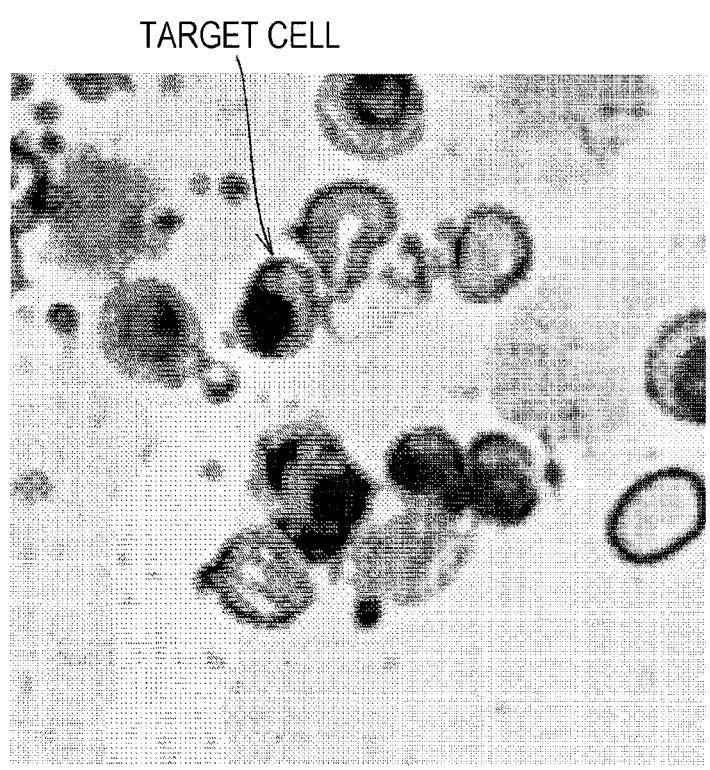
FIG. 2 is an illustration showing an example of a test image captured by an optical microscope.

The image processing device 4 acquires a captured image image-captured by the optical microscope 2 (hereinafter, referred to as test image). FIG. 2 shows an example of a test image. As shown in FIG. 2, the test image includes images of various cells included in the maternal red blood cells. A cell having a nucleus colored in a dark color is a target cell. It is to be noted that the nucleus of a target cell (nucleated red blood cell) is dyed in a slightly darker color than the color of the nucleus of the other cell by May-Giemsa stain.

Also, the image processing device 4 sets plural display subject regions each possibly including a target cell in the captured image. A list of the images of the set display subject regions is displayed on the display 6.

Figure 3:
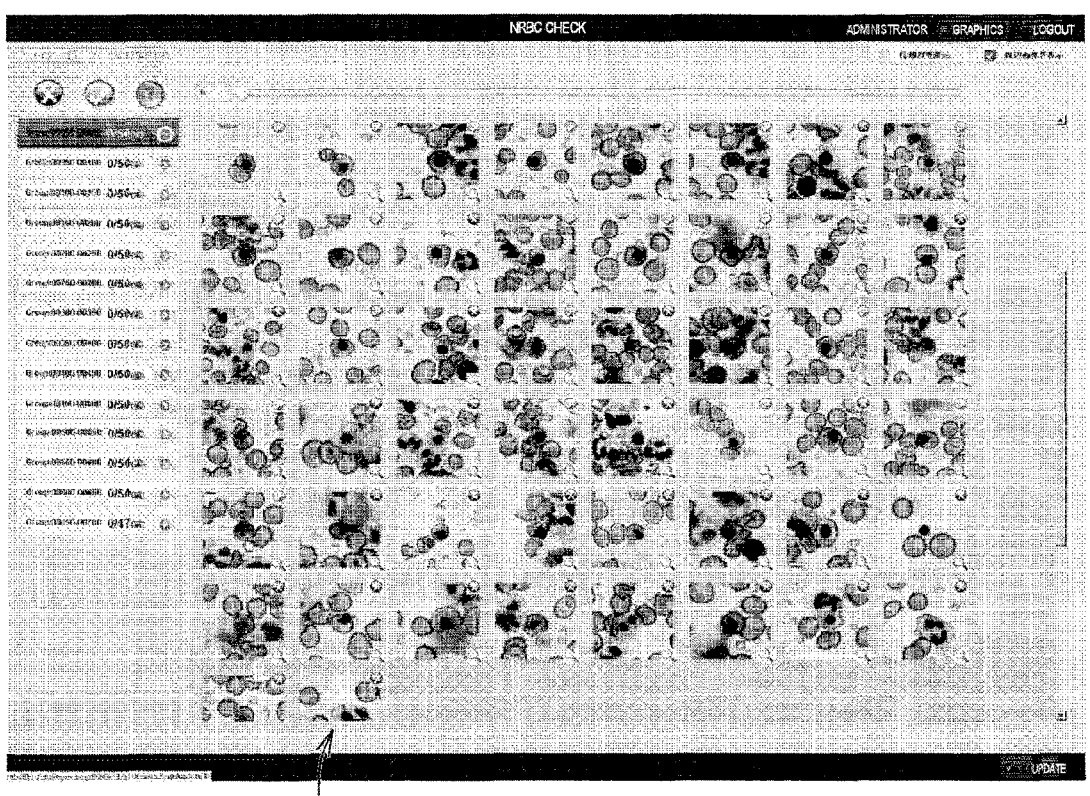
FIG. 3 is an illustration showing a list of images of display subject regions displayed on a display.

The display 6 displays a screen on the basis of the result of processing by the image processing device 4. In this exemplary embodiment, the display 6 displays the list of images of the respective display subject regions. FIG. 3 shows an example of a list of images of display subject regions displayed on the display 6. A user (for example, doctor) references each image, and searches for a number of target cells required for, for example, a prenatal diagnosis.

This image processing system 1 takes a measure to decrease the number of images to be referenced to find out the required number of target cells. That is, for each display subject region, probability that the image is an image of a target cell is calculated. An image with higher calculated probability is displayed at an upper side. Also, calculation accuracy of probability is increased so that the probability is more highly evaluated as the image has higher probability that the image is of a target cell.

A technology is described below which decreases the number of images to be referenced to find out the required number of target cells while increasing the calculation accuracy of probability.

Figure 4:
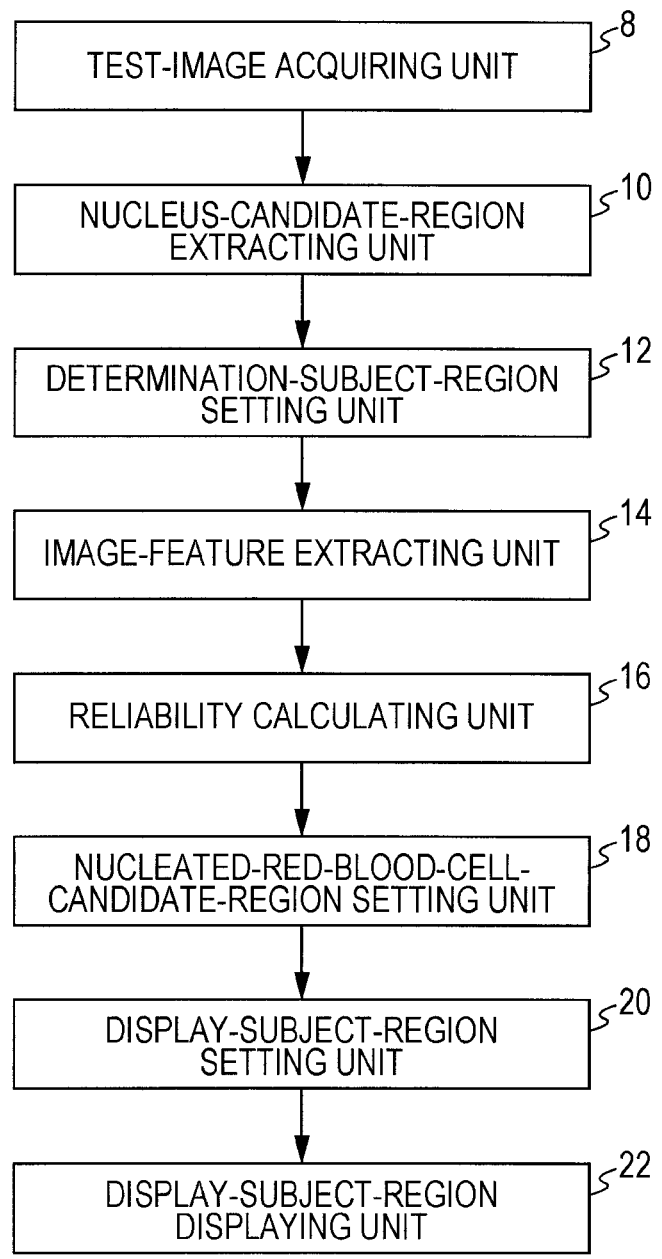
FIG. 4 is a functional block diagram showing a function group provided by an image processing device.

FIG. 4 is a functional block diagram showing a function group provided by the image processing device 4. Provided in the image processing device 4 are a test-image acquiring unit 8, a nucleus-candidate-region extracting unit 10, a determination-subject-region setting unit 12, an image-feature extracting unit 14, a reliability calculating unit 16, a nucleated-red-blood-cell-candidate-region setting unit 18, a display-subject-region setting unit 20, and a display-subject-region displaying unit 22. These functions are provided when a computer including control means such as a microprocessor, storage means such as a memory, input/output means for transmitting/receiving data to/from an external device, etc., reads and executes a program stored in a computer-readable information storage medium (for example, optical disc, magnetic disk, magnetic tape, magneto-optical disk, flash memory, or the like). Alternatively, the program may be supplied to the image processing device 4 being the computer through a data communication network such as the Internet.

Respective functions are described below. The test-image acquiring unit 8 acquires data of a test image (see FIG. 2) captured by the optical microscope 2 from the optical microscope 2.

Figure 5:
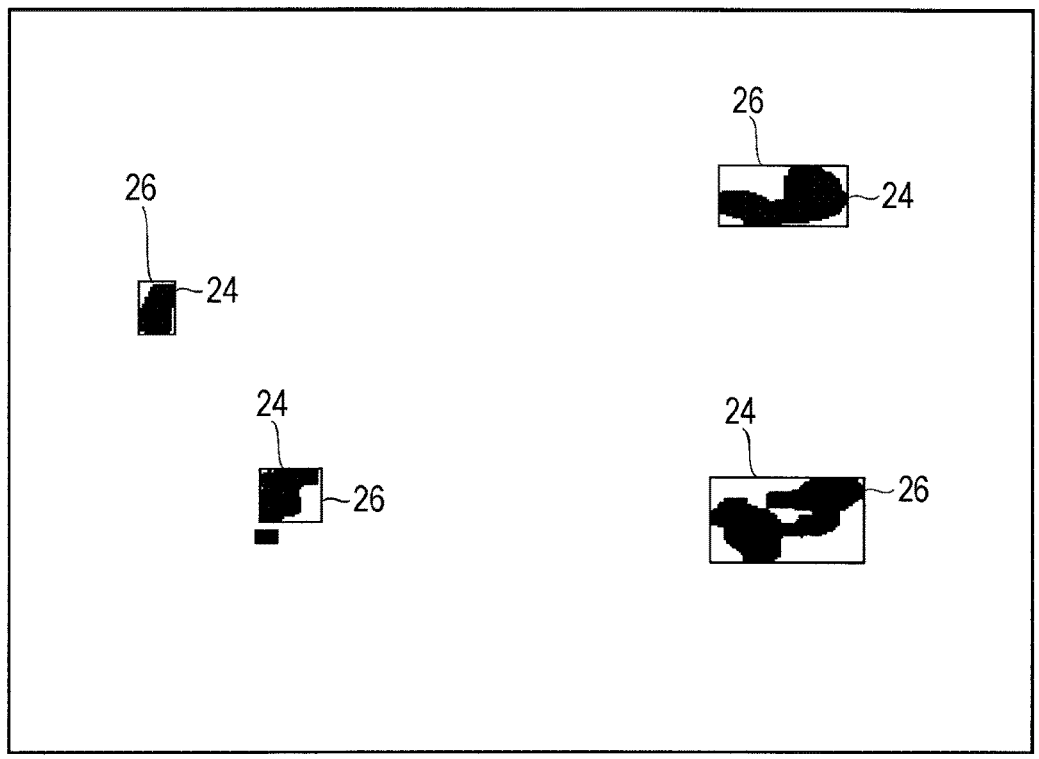
FIG. 5 is an illustration showing an example of pixel blocks and nucleus candidate regions extracted from a test image.

The nucleus-candidate-region extracting unit 10 extracts nucleus candidate regions each included in the test image and corresponding to a nucleus of a target cell. For example, the nucleus-candidate-region extracting unit 10 extracts pixel blocks 24 of significant pixels included in the test image. In this case, the significant pixels are pixels with density values being equal to or larger than a threshold. Then, the nucleus-candidate-region extracting unit 10 specifies a circumscribing rectangular region of each pixel block 24 as a nucleus candidate region 26, and acquires coordinate data indicating the specified nucleus candidate region 26. FIG. 5 shows an example of pixel blocks 24 and nucleus candidate regions 26 extracted from the test image. Black solid portions indicate the pixel blocks 24.

Figure 6:
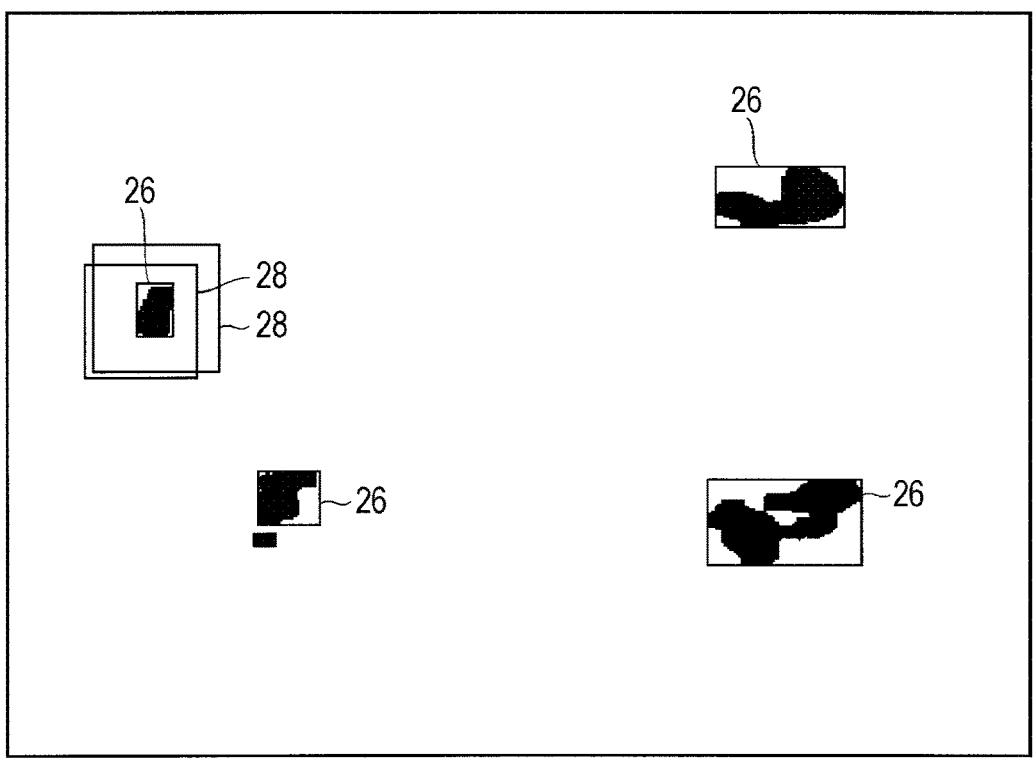
FIG. 6 is an illustration showing an example of determination subject regions.

The determination-subject-region setting unit 12 sets a rectangular region centered at each single pixel of the pixels included in each nucleus candidate region 26 as a determination subject region 28. A single determination subject region 28 may be set for a single pixel, or plural determination subject regions 28 with different sizes may be set for a single pixel. In this exemplary embodiment, the determination subject region 28 has at least the same size as the nucleus candidate region 26. FIG. 6 shows an example of the determination subject regions 28. FIG. 6 shows determination subject regions 28 centered at a pixel in an upper left nucleus candidate region 26.

The image-feature extracting unit 14 extracts, for each determination subject region 28, an image feature amount of an image of the determination subject region 28. For example, the image-feature extracting unit 16 calculates a HOG (Histogram Oriented Gradients) feature amount of an image of each determination subject region 28.

In this case, the image-feature extracting unit 14 obtains, for each pixel in the determination subject region 28, a brightness gradient vector of the pixel. The brightness gradient vector includes the angle indicating the orientation (brightness gradient orientation) and the magnitude (brightness gradient intensity). Also, the image-feature extracting unit 14 sets a number Y of block regions each including a number X of cell regions in the determination subject region 28, and obtains a brightness gradient orientation histogram for each cell region forming each block region. The brightness gradient orientation histogram has 9 angle ranges formed by dividing the angle range from 0 to 180 degrees into 9 sections (hereinafter, written as bins), and a brightness gradient vector of each pixel in a cell is sorted into a bin corresponding to the orientation of the vector. Also, the total sum of the magnitudes of the brightness gradient vectors sorted into the bin is calculated as the degree of the bin.

Then, normalization is performed on a block region basis so that the mean square of the brightness gradient orientation histogram obtained for each cell region becomes 1. A value of "9×X" created by linking normalized brightness gradient orientation histograms in a block region is calculated as a feature amount of the block region, and a value of "9×X×Y" created by linking all block regions is calculated as a HOG feature amount of the determination subject region 28.

Alternatively, the image-feature extracting unit 14 may calculate a Cell-HOG feature amount which is described later. In this case, unlike the HOG feature amount, a brightness gradient orientation histogram having 18 bins obtained by dividing the angle range from 0 to 360 degrees into 18 sections is obtained. Also, without normalization of a brightness gradient orientation histogram obtained for each cell region, a value of "18×X" created by linking brightness gradient orientation histograms in a block region is calculated as a feature amount of the block region. Also, a value of "18×X×Y" created by linking all block regions is calculated as a Cell-HOG feature amount of the determination subject region.

The reliability calculating unit 16 acquires, for each determination subject region 28, a numerical value indicating probability that an image in the determination subject region 28 is an image of a target cell (hereinafter, written as reliability) on the basis of the image feature amount of the image of the determination subject region 28. The reliability corresponds to basic probability information.

To be specific, the reliability calculating unit 16 acquires an output value when an image feature amount of the image of the determination subject region 28 is input to an identifier previously generated by a learning algorithm, as reliability. As the value of reliability is larger, probability that the image in the determination subject region 28 is an image of a target cell is increased. In this case, an identifier generated by learning each image feature amount of each of a number N of sample images according to AdaBoost Algorithm is used. In this exemplary embodiment, gentle AdaBoost is used as AdaBoost Algorithm. However, it is not limited thereto. For example, AdaBoost Algorithm may use discrete AdaBoost Algorithm. Alternatively, an identifier generated by another learning algorithm instead of Ada-Boost Algorithm may be used.

AdaBoost Algorithm is briefly described. In this case, an example is employed in which an identifier is created through learning from a number N pieces of data while a feature amount is $x_i$ and a classification label is $y_i$ ($y_i \in \{-1, 1\}$) by using Gentle AdaBoost Algorithm. In Gentle AdaBoost Algorithm, while an initial value of a weight $w_i$ that is given to each data is "1/N" and an initial value of an identifier F(x) is "0," an optimal weak identifier $f_m(x)$ is selected from various regression trees, and the identifier F(x) and the weight $w_i$ are updated by using Expression (1) and Expression (2) as follows. Also, after $w_i$ is updated, normalization is performed so that the total sum of $w_i$ becomes "1."

$$F(x) \leftarrow F(x) + f_m(x) \qquad \text{Expression (1)}$$

$$w_i \leftarrow w_i \cdot \exp(-y_i f_m(x_i)) \qquad \text{Expression (2)}$$

In this case, when the optimal weak identifier is selected, a tree $f_m(x)$ with an expected value $E[\exp(-y \cdot F(x))]$ of a weighted error of the identifier $F(x)$ being the minimum is selected. The weak identifier $f_m(x)$ is expressed by Expression (3) as follows.

$$f_m(x) = P_w(y=1|x) - P_w(y=-1|x) \qquad \text{Expression (3)}$$

In this case, $P_w(y=1|x)$ and $P_w(y=-1|x)$ are probability values weighted with w. $P_w(y=-1|x)$ is obtained by dividing the total value of weights w of Positive data in a leaf node to which x belongs by the total value of weights w of all data in the leaf node. Also, $P_w(y=-1|x)$ is obtained by dividing the total value of weights w of Negative data in a leaf node to which x belongs by the total value of weights w of all data in the leaf node.

Then, update of the identifier $F(x)$ and the weight $w_i$ is performed a number M times on the basis of Expression (1) to Expression (3), and thus the identifier $F(x)$ indicated by Expression (4) is obtained.

$$F(x) = \Sigma_{m=1 \ to \ M} f_m(x) \qquad \text{Expression (4)}$$

The nucleated-red-blood-cell-candidate-region setting unit 18 sets a nucleated red blood cell candidate region with probability that a target cell is included being a predetermined level or higher. That is, the nucleated-red-blood-cell-candidate-region setting unit 18 sets the determination subject region 28 with reliability being a threshold or higher as a nucleated red blood cell candidate region. Alternatively, all determination subject regions 28 may be set as nucleated red blood cell candidate regions.

Figure 7:
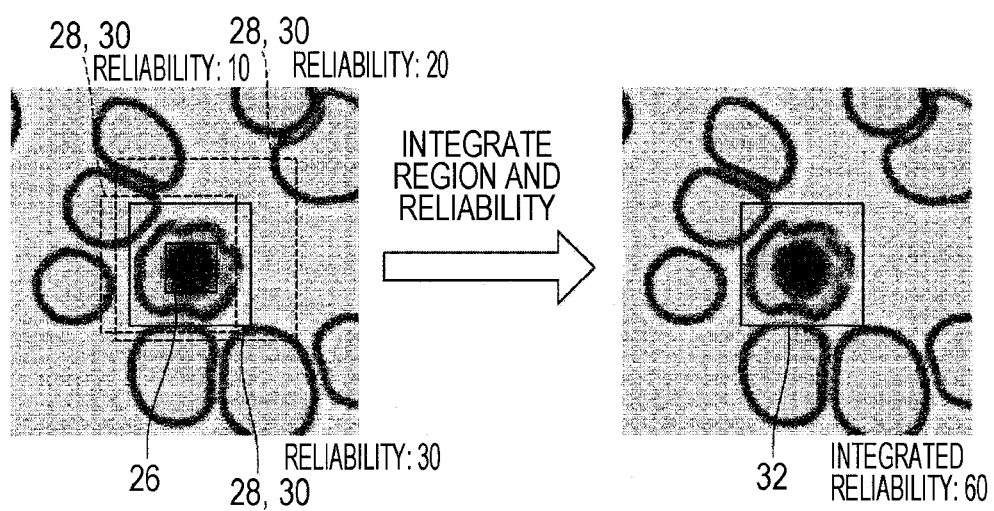
FIG. 7 is an illustration for describing a setting method of a display subject region.

The display-subject-region setting unit 20 sets a display subject region corresponding to each nucleus candidate region 26. That is, the display-subject-region setting unit 20 sets a display subject region corresponding to a nucleus candidate region 26 on the basis of plural nucleated red blood cell candidate regions that at least partly overlap the nucleus candidate region 26. To be specific, the display-subject-region setting unit 20 sets a display subject region corresponding to a nucleus candidate region 26 so as to set a nucleated red blood cell candidate region with the maximum reliability among plural nucleated red blood cell candidate regions that at least partly overlap the nucleus candidate region 26 as a display subject region. FIG. 7 is an illustration for describing a setting method of a display subject region. In FIG. 7, a nucleated red blood cell candidate region 30 with reliability of "10," a nucleated red blood cell candidate region 30 with reliability of "20," and a nucleated red blood cell candidate region 30 with reliability of "30" are set for a nucleus candidate region 26. In this case, the nucleated red blood cell candidate region 30 with reliability of "30" is set as a display subject region 32. Alternatively, a region including a plurality of nucleated red blood cell candidate regions 30 that at least partly overlap a nucleus candidate region 26 may be set as a display subject region 32 corresponding to the nucleus candidate region 26.

If there is no nucleated red blood cell candidate region 30 that at least partly overlaps a nucleus candidate region 26, a display subject region 32 corresponding to the nucleus candidate region 26 is not set.

Also, the display-subject-region setting unit 20 not only sets a display subject region 32, but also calculates a numerical value indicating probability that an image in the display subject region 32 is an image of a target cell (hereinafter, written as integrated reliability). The integrated reliability corresponds to probability information. To be specific, the display-subject-region setting unit 20 calculates, on the basis of reliabilities of plural nucleated red blood cell candidate regions 30 that at least partly overlap a nucleus candidate region 26, integrated reliability of a display subject region 32 corresponding to the nucleus candidate region 26. For example, the display-subject-region setting unit 26 calculates the maximum reliability among the reliabilities of the plural nucleated red blood cell regions 30 that at least partly overlap the nucleus candidate region 26 as integrated reliability of a display subject region 32 corresponding to the nucleus candidate region 26. Alternatively, for example, the display-subject-region setting unit 20 calculates an increasing function value that uses reliabilities of plural nucleated red blood cell regions 30 that at least partly overlap a nucleus candidate region 26 as variables (for example, the total sum of respective variables or the average of respective variables), or an increasing function value that uses the maximum reliability among the reliabilities of the plural nucleated red blood cell candidate regions 30 and the number of the plural nucleated red blood cell candidate regions 30 as variables (for example, the product of the respective variables or the power of the other variable while one variable serves as the exponent), as integrated reliability of a display subject region 32 corresponding to the nucleus candidate region 26. In FIG. 7, the total sum of reliabilities of three nucleated red blood cell candidate regions 30 is calculated as integrated reliability.

Alternatively, the display-subject-region setting unit 20 may set plural display subject regions 32 for a single nucleus candidate region 26. For example, a case is expected in which a portion of plural nucleated red blood cell candidate regions 30 that at least partly overlap a nucleus candidate region 26 serves as an independent nucleated red blood cell candidate region 30 (a nucleated red blood cell candidate region 30 that does not overlap any other nucleated red blood cell candidate region 30), and a residual portion is a non-independent nucleated red blood cell candidate region 30. In this case, the independent nucleated red blood cell candidate region 30 and a nucleated red blood cell candidate region 30 having the maximum reliability among non-independent nucleated red blood cell candidate regions 30 may be respectively set as display subject regions 32. In this case, reliability of the independent nucleated red blood cell candidate region 30 may serve as integrated reliability of one display subject region 32. Also, integrated reliability of the other display subject region 32 may be calculated on the basis of reliabilities of the respective non-independent nucleated red blood cell candidate regions 30. For example, the maximum reliability among the reliabilities of the non-independent nucleated red blood cell candidate regions 30, an increasing function value that uses the respective reliabilities as variables, or an increasing function value that uses the maximum reliability among the respective reliabilities and the number of the non-independent red blood cell candidate regions 30 as variables may serve as integrated reliability of the other display subject region 32.

The display-subject-region displaying unit 22 cuts out images in the respective display subject regions from the test image, and causes the display 6 to display the list of the images of the respective display subject regions. At this time, the display-subject-region displaying unit 22 displays the images of the respective display subject regions in the descending order of the integrated reliability. In other words, an image with higher integrated reliability is displayed with higher priority.

In this image processing device 4, acquired as integrated reliability of a display subject region 32 corresponding to a nucleus candidate region 26 is an increasing function value that uses reliabilities of plural nucleated red blood cell candidate regions 30 that at least partly overlap a nucleus candidate region 26 as variables, or an increasing function value that uses any of the reliabilities of the plural nucleated red blood cell candidate regions 30 and the number of the nucleated red blood cell candidate regions 30 as variables. Hence, calculation accuracy of probability that an image in a display subject region 32 is an image of a target cell is increased. In fact, as compared with a case in which the maximum reliability among the reliabilities of the respective nucleated red blood cell candidate regions 30 is used as integrated reliability, a result is obtained in which the number of images that are not an image of a target cell but included in images displayed at a higher order is decreased.

Figure 8:
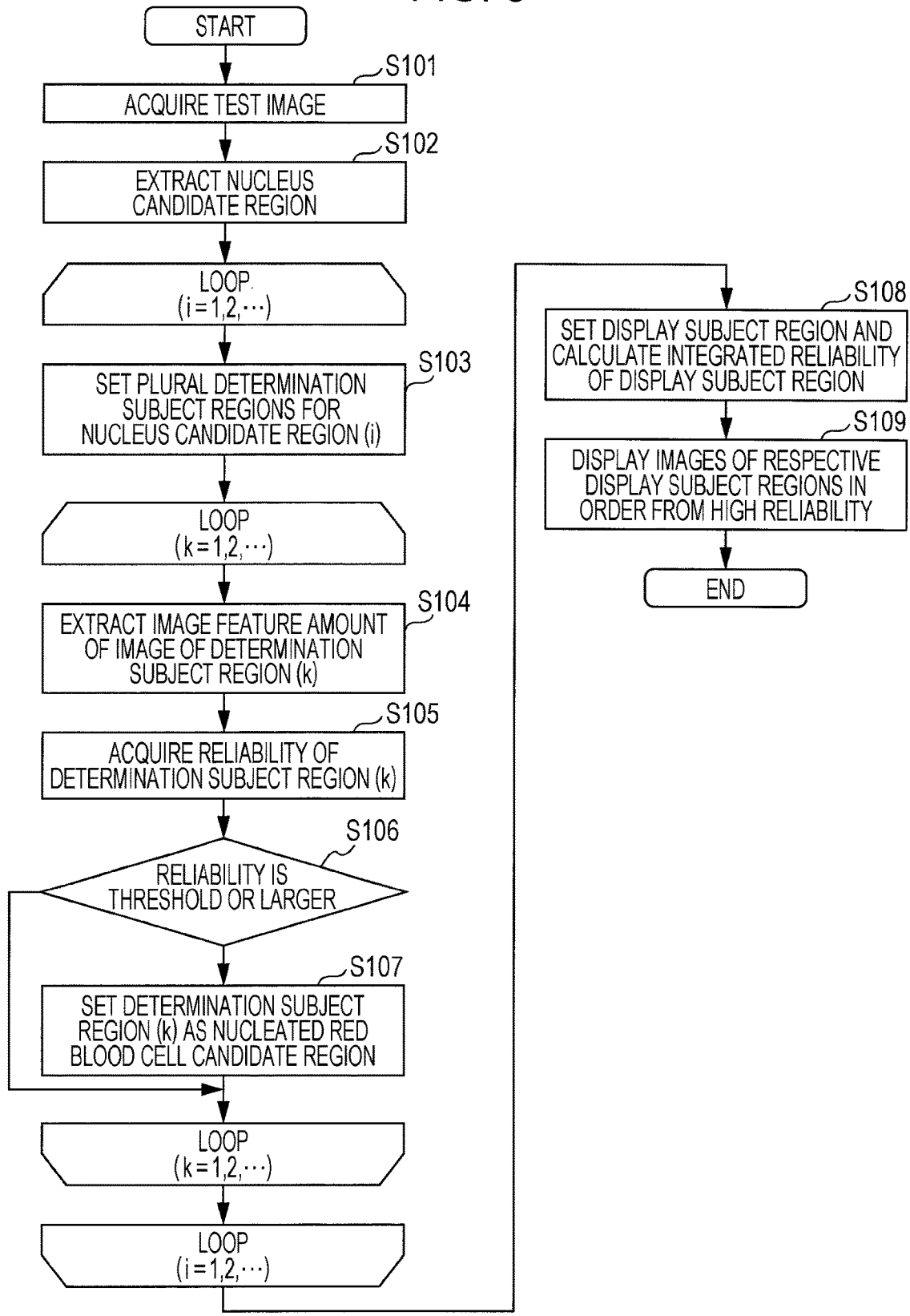
FIG. 8 is a flowchart showing an example of processing executed by the image processing device.

FIG. 8 is a flowchart showing an example of processing executed by the image processing device 4. First, the image processing device 4 acquires a test image (see FIG. 2) from the optical microscope 2 (S101). Then, the image processing device 4 extracts pixel blocks 24 of significant pixels included in the test image, and extracts a circumscribing rectangular region of each pixel block 24 as a nucleus candidate region 26 (S102). Also, the image processing device 4 causes storage means to store coordinate data indicating a range of each nucleus candidate region 26.

Then, the image processing device 4 sequentially selects respective nucleus candidate regions 26 one by one as nucleus candidate regions (i), and executes steps from S103 to S107 for each nucleus candidate region (i). That is, the image processing device 4 sets plural determination subject regions 28 centered at a pixel in a nucleus candidate region 26 (i), and causes the storage means to store coordinate data indicating the ranges of the set determination subject regions 28 (S103). Then, the image processing device 4 sequentially selects the determination subject regions 28 set in S103 one by one as determination subject regions (k), and executes steps from S104 to S107 for each determination subject region (k).

That is, the image processing device 4 cuts out an image of a determination subject region (k) from the test image, and extracts an image feature amount (for example, HOG feature amount) of an image of the determination subject region (k) (S104). Then, the image processing device 4 inputs the image feature amount extracted in S104 to an identifier, and acquires an output value of the identifier as reliability of the determination subject region (k) (S105). Also, the image processing device 4 causes the storage means to store the reliability of the determination subject region (k) in association with coordinate data of the determination subject region (k). Then, the image processing device 4 determines whether or not the reliability of the determination subject region (k) is a threshold or larger (S106). If the reliability of the determination subject region (k) is smaller than the threshold (N in S106), the image processing device 4 selects the next determination subject region 28 as a determination subject region (k), and executes the steps in S104 and later again. In contrast, if the reliability of the determination subject region (k) is the threshold or larger (Y in S106), the image processing device 4 sets the determination subject region (k) as a nucleated red blood cell candidate region 30 (S107). For example, the image processing device 4 causes the storage means to store a flag value "0" in association with coordinate data of the determination subject region (k) in S107. Then, the image processing device 4 selects the next determination subject region 28 as a determination subject region (k), and executes the steps in S104 and later again.

By the processing to S107, the nucleated red blood cell candidate region 30 is specified.

Then, the image processing device 4 sets a display subject region 32, and calculates integrated reliability of the display subject region 32 (S108). To be specific, the image processing device 4 executes the following processing for each nucleus candidate region 26 in S108. That is, the image processing device 4 specifies nucleated red blood cell candidate regions 30 that at least partly overlap a nucleus candidate region 26 (nucleated red blood cell candidate regions 30 centered at a pixel in a nucleus candidate region 26) on the basis of the stored content in the storage means, and sets a nucleated red blood cell candidate region 30 having the maximum reliability among the specified nucleated red blood cell candidate regions 30 as a display subject region 32. For example, the image processing device 4 updates the flag value associated with the coordinate data of the nucleated red blood cell region 30 set as the display subject region 32 to "1" in S108. Also, the image processing device 4 calculates the total sum of the reliabilities of the specified nucleated red blood cell candidate regions 30 as integrated reliability, and causes the storage means to store the calculated integrated reliability in association with the coordinate data of the display subject region 32.

The image processing device 4 cuts out an image of each display subject region 32 from the test image at a predetermined timing (for example, at a timing in which a user performs a predetermined operation), and causes the display 6 to display the list of images of respective display subject regions 32 in the descending order of the integrated reliability (S109).

The exemplary embodiment of the invention is not limited to the above-described exemplary embodiment. For example, the case, in which a nucleated red blood cell is a target cell, has been described above; however, a cell other than a nucleated red blood cell may be a target cell. That is, the invention may be applied even if a cell other than a nucleated red blood cell is a target cell.

Figure 9:
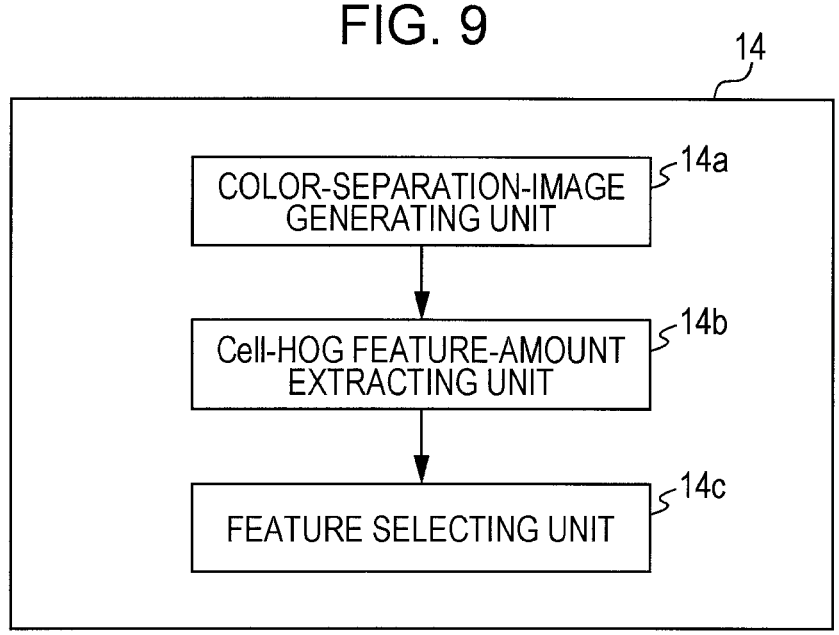
FIG. 9 is an illustration showing a configuration example of an image-feature-amount extracting unit.

Also, for example, the image-feature extracting unit 14 may extract Cell-HOG feature amounts from respective color separation images of an image of a determination subject region 28, and may select a number L of components in total from among components of the Cell-HOG feature amount extracted from each color separation image, as an image feature amount of the image of the determination subject region 28. For example, as shown in FIG. 9, the image-feature extracting unit 14 may include a color-separation-image generating unit 14a, a Cell-HOG feature-amount extracting unit 14b, and a feature selecting unit 14c.

Figure 10:
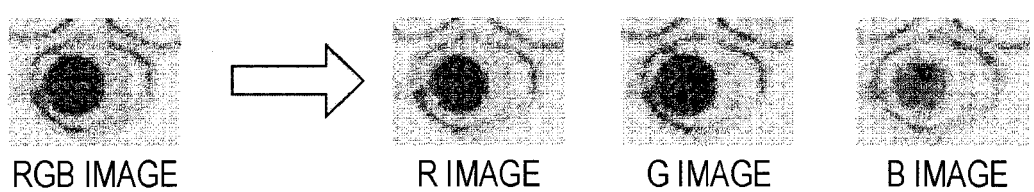
FIG. 10 is an illustration showing a state in which color separation images are generated.

In this case, the color-separation-image generating unit 14a generates color separation images of an image of a determination subject region 28. FIG. 10 shows a state in which color separation images (R image, G image, B image) of an image (RGB image) of a determination subject region 28 are generated. In this case, color separation is performed in the RGB color space; however, color separation may be performed in other color space (for example, Lab, HSV). Also, the Cell-HOG feature-amount extracting unit 14b extracts a Cell-HOG feature amount from each color separation image.

Then, the feature selecting unit 14c selects a number L of components in total from the Cell-HOG feature amount extracted from each color separation image as an image feature amount of the image of the determination subject image 28. For example, for each color component, the feature selecting unit 14c may compare a histogram expressed by a Cell-HOG feature amount obtained from a positive example image of the color component with a histogram expressed by a Cell-HOG feature amount obtained from a negative example image of the color component, and may select a number L of components corresponding to a bin with a low degree of overlapping. Alternatively, for example, the feature selecting unit 14c may select a number L of components according to a learning algorithm.

The invention claimed is:

1. An image processing device comprising
a nucleus-candidate-region extracting unit that extracts, from a captured image obtained by image-capturing a sample piece including a target cell having a nucleus, a nucleus candidate region corresponding to the nucleus;
a basic-probability-information acquiring section that acquires, for each of a plurality of determination subject regions determined on the basis of the nucleus candidate region extracted by the nucleus-candidate-region extracting unit, basic probability information indicating probability that an image in the determination subject region is an image of the target cell, on the basis of a feature amount of the image of the determination subject region; and
a probability-information calculating section that calculates probability information indicating probability that an image in a display subject region corresponding to the nucleus candidate region is the image of the target cell, on the basis of the basic probability information acquired for each of the plurality of determination subject regions,
wherein the probability-information calculating section calculates, as the probability information indicating the probability that the image in the display subject region corresponding to the nucleus candidate region is the image of the target cell, an increasing function value that uses the basic probability information acquired for each of the plurality of determination regions as a variable, or an increasing function value that uses the basic probability information acquired for any of the plurality of determination regions and the number of the plurality of determination subject regions as variables.

2. The image processing device according to claim 1, wherein the basic-probability-information acquiring section
acquires, for each nucleus candidate region extracted by the nucleus-candidate-region extracting unit, the basic probability information for each of the plurality of determination subject regions determined on the basis of the nucleus candidate region,
wherein the probability-information calculating section calculates, for each nucleus candidate region extracted by the nucleus-candidate-region extracting unit, the probability information indicating the probability that the image in the display subject region corresponding to the nucleus candidate region is the image of the target cell, and
wherein the image processing device further includes
a display section that displays an image of each display subject region in a descending order of the probability indicated by the probability information.

3. The image processing device according to claim 1, wherein the basic-probability-information acquiring section acquires a value obtained by inputting a feature amount of the image of the determination subject region to an identifier generated by a learning algorithm, as the basic probability information indicating the probability that the image in the determination subject region is the image of the target cell.

4. The image processing device according to claim 1, further comprising:
a setting unit that sets a display target region corresponding to the nucleus candidate region, on the basis of a plurality of determination subject regions determined on the basis of the nucleus candidate region.

5. The image processing device according to claim 4, wherein the setting unit
sets a determination subject region from which basic probability information having maximum probability among the plurality of determination subject regions determined on the basis of the nucleus candidate region, as a display target region corresponding to the nucleus candidate region.

6. The image processing device according to claim 1, wherein the probability-information calculating section
calculates a sum of the basic probability information acquired for each of the plurality of determination subject regions, as the probability information indicating the probability that the image in the display subject region corresponding to the nucleus candidate region is the image of the target cell.

7. A non-transitory computer readable storage medium storing a program causing a computer to execute a process, the process comprising:
extracting, from a captured image obtained by image-capturing a sample piece including a target cell having a nucleus, a nucleus candidate region corresponding to the nucleus;
acquiring, for each of a plurality of determination subject regions determined on the basis of the extracted nucleus candidate region, basic probability information indicating probability that an image in the determination subject region is an image of the target cell, on the basis of a feature amount of the image of the determination subject region; and
calculating probability information indicating probability that an image in a display subject region corresponding to the nucleus candidate region is the image of the target cell, on the basis of the basic probability information acquired for each of the plurality of determination subject regions,
wherein
the calculating calculates, as the probability information indicating the probability that the image in the display subject region corresponding to the nucleus candidate region is the image of the target cell, an increasing function value that uses the basic probability information acquired for each of the plurality of determination regions as a variable, or an increasing function value that uses the basic probability information acquired for any of the plurality of determination regions and the number of the plurality of determination subject regions as variables.

8. An image processing method comprising:
extracting, from a captured image obtained by image-capturing a sample piece including a target cell having a nucleus, a nucleus candidate region corresponding to the nucleus;
acquiring, for each of a plurality of determination subject regions determined on the basis of the extracted nucleus candidate region, basic probability information indicating probability that an image in the determination subject region is an image of the target cell, on the basis of a feature amount of the image of the determination subject region; and calculating probability information indicating probability that an image in a display subject region corresponding to the nucleus candidate region is the image of the target cell, on the basis of the basic probability information acquired for each of the plurality of determination subject regions, wherein the calculating calculates, as the probability information indicating the probability that the image in the display subject region corresponding to the nucleus candidate region is the image of the target cell, an increasing function value that uses the basic probability information acquired for each of the plurality of determination regions as a variable, or an increasing function value that uses the basic probability information acquired for any of the plurality of determination regions and the number of the plurality of determination subject regions as variables.

\* \* \* \* \*